United States Patent
Streckel et al.

(10) Patent No.: US 6,541,650 B2
(45) Date of Patent: Apr. 1, 2003

(54) PROCESS FOR PREPARING SILANES

(75) Inventors: Willi Streckel, Mehring-Oed (DE); Wilfried Kalchauer, Burghausen (DE); Herbert Straussberger, Mehring-Oed (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/137,949

(22) Filed: May 3, 2002

(65) Prior Publication Data

US 2002/0183537 A1 Dec. 5, 2002

(30) Foreign Application Priority Data

May 31, 2001 (DE) .......................... 101 26 558

(51) Int. Cl.$^7$ .............................. C07F 7/08; C07F 7/16
(52) U.S. Cl. ....................................... 556/466; 423/344
(58) Field of Search ........................... 423/344; 552/466

(56) References Cited

U.S. PATENT DOCUMENTS 5,288,892 A * 2/1994 Pachaly et al. ............. 556/466
5,292,909 A   3/1994 Chadwick et al.
5,877,337 A * 3/1999 Mautner et al. ............ 556/466

FOREIGN PATENT DOCUMENTS

EP    0 634 417 A1    1/1995
EP    0 869 129 A1   10/1998

OTHER PUBLICATIONS

Caplus–Abstract Corresponding To JP–A 11092130 [AN 1999:225513].
Caplus–Abstract Corresponding To BR–A 8 006 892 [AN 1983:200732].
Derwent Abstract Corresponding To EP–A 634417 [AN 1998–507568].
Caplus–Abstract Corresponding To JP–A 07206421 [AN 1995:922114].
Caplus–Abstract Corresponding To BR–A 9 002 380 [AN 1993:41833].
K.L. Lewis/D.G. Rethwisch, "Catalyzed Direct Reactions of Silicon", Elsevier 1993, pp. 1–66 and 441–457.

* cited by examiner

Primary Examiner—Paul F. Shaver
(74) Attorney, Agent, or Firm—Brooks & Kushman P.C.

(57) ABSTRACT

A process for preparing silanes of the formula 1:

$$R_a SiH_b Cl_{4-a-b} \qquad (1)$$

where
R is methyl or ethyl,
a is 0, 1, 2 or 3 and
b is 0 or 1,
from hydrogen chloride gas and reactants selected from among
a) silicon metal,
b) disilanes and oligosilanes whose radicals are selected from among H, R and Cl,
and mixtures thereof, wherein the hydrogen chloride gas is prepared from $H_2$ and $Cl_2$ in a concerted process.

19 Claims, No Drawings

PROCESS FOR PREPARING SILANES

BACKGROUND OF THE INVENTION

1. Field of the Invention

The invention relates to a process for preparing silanes from hydrogen chloride gas and silicon metal, disilanes, and oligosilanes as reactants.

2. Background Art

In the preparation of chlorosilanes, silicon is reacted with hydrogen chloride gas, if appropriate in the presence of catalysts, resulting, depending on the reaction conditions, in the formation of trichlorosilane or tetrachlorosilane as the main product. The reaction temperature selected depends greatly on the desired target product ($HSiCl_3$ or $SiCl_4$) and is normally from 230° C. to several hundred ° C. Trichlorosilane is used, for example, for the preparation of high-purity silicon or the preparation of (organo)functional silanes, while tetrachlorosilane is used, for example, in the preparation of pyrogenic silica. The relevant technology is described in *Catalyzed Direct Reactions of Silicon*, edited by K. L. Lewis and D. G. Rethwisch, Ed.s Elsevier 1993; "Commercial Production of Silanes by Direct Synthesis," pages 1–66 and "Direct Synthesis of Chlorosilanes and Silane," pages 441–457.

In the direct synthesis of methylchlorosilanes by the Muller-Rochow method (direct synthesis), silicon is reacted with methyl chloride in the presence of catalysts and promoters to form dimethyldichlorosilane, with higher-boiling methylchlorodisilanes and methylchlorooligosilanes and the corresponding siloxanes and carbosilanes also being formed as by-products. Lewis, *op. cit.*, pp. 1–66. U.S. Pat. No. 5,877,337 describes a process in which solids-containing residues from the direct synthesis of organochlorosilanes are worked up at low pressures and the organosilicon components are converted into useful silanes. This objective is achieved by carrying out thermal cracking of the residues from the direct synthesis in the presence of hydrogen chloride in a tube reactor containing rotating internals at temperatures of 300–800° C. The rotary motion of the internals shears off deposits on the reactor walls caused by carbon formation or solid components. This is said to prevent blocking of the reactor.

In these processes, hydrogen chloride gas is required and the reactions are carried out at relatively high temperatures. The hydrogen chloride gas is taken from appropriate storage tanks and may have to be preheated. In Lewis, *op. cit.*, for example, it is stated on page 6 that liquid anhydrous hydrogen chloride which is used in the direct synthesis of chlorosilanes is typically transported to production sites in cooled tank cars. HCl is vaporized, heated to about 200° C. and subsequently introduced into the reactor.

The preparation of HCl from the elements is known. $H_2$ and $Cl_2$ are introduced separately into a combustion chamber, mixed and reacted in a burner flame. The reaction is strongly exothermic, so that flame temperatures of above 2000° C. are possible. The hydrogen chloride gas is subsequently cooled by means of appropriate cooling apparatuses.

SUMMARY OF THE INVENTION

The present invention avoids all or a portion of the energy penalty required to heat hydrogen chloride gas prior to the commercial preparation of silanes by the in situ generation of hydrogen chloride by combustion of hydrogen and chlorine. Numerous advantages other than thermal efficiency surprisingly accrue from this process.

DETAILED DESCRIPTION OF THE PREFERRED EMBODIMENT(S)

The invention provides a process for preparing silanes of the formula 1:

$$R_aSiH_bCl_{4-a-b} \quad (1)$$

where

R is methyl or ethyl, a is 0, 1, 2 or 3 and b is 0 or 1, from hydrogen chloride gas and reactants selected from among a) silicon metal and b) disilanes and oligosilanes whose radicals are selected from among H, R and Cl, and from mixtures thereof, wherein the hydrogen chloride gas is prepared from $H_2$ and $Cl_2$ in the same process step. The disilanes and oligosilanes preferably bear only radicals R and Cl.

The process has the advantages that hydrogen chloride does not have to be transported and/or stored and preheated; that a higher degree of conversion and/or shorter reaction times can be achieved due to the higher temperatures; that relatively high reaction temperatures can be achieved very simply; that two separate plants do not have to be built and operated; that the process can be carried out simply, since no moving parts are necessary; that when using methylsilanes as starting materials, the undesirable decomposition reactions occur to a lesser extent; and that the energy required for the reaction does not have to be introduced via hot reactor walls and therefore the reactor is subjected to lesser thermal stress. It is thus possible to employ less expensive reactor construction materials since energy does not have to be introduced via the reactor walls.

The preparation of the silanes of the formula 1 and the preparation of the hydrogen chloride gas from $H_2$ and $Cl_2$ is a concerted reaction, and preferably occurs in one reaction zone. For example, the reactants (a) and/or (b) are preferably fed together with $H_2$ and $Cl_2$ into a plant for producing HCl and reacted in this way. The term "concerted" implies that preparation of hydrogen chloride and its further reaction occur without first separating the hydrogen chloride produced in situ.

The preparation of the hydrogen chloride gas from $H_2$ and $Cl_2$ is preferably carried out in a combustion tube. The length of the combustion tube is preferably designed so that the residence time of the reaction gases in the hot reaction region is from 1 to 30 seconds, preferably from 2 to 20 seconds, most preferably from 3 to 15 seconds. The gas velocity in the combustion tube is preferably selected so that no deposits occur in the tube.

In addition to the hydrogen chloride gas produced from $H_2$ and $Cl_2$ in the same process step, it is also possible to feed additional, pre-synthesized hydrogen chloride gas in as a reactant (c). The maximum amount of HCl added is selected so that the temperature in the region of the reaction of hydrogen chloride gas with the other reactants is preferably at least 400° C., more preferably at least 500° C., and most preferably at least 600° C. In this case, the added HCl simultaneously serves as a cooling medium, i.e. the flame temperature is thereby adjusted to the desired reaction temperature.

However, it is also possible to use other substances which are inert under these conditions as a cooling medium. Preference is given to using chlorosilanes, for example silicon tetrachloride, or excess hydrogen, based on the reaction $H_2+Cl_2 \rightarrow 2$ HCl, since these substances are present in the reaction system in any case.

The mixing ratio of $H_2$ to $Cl_2$ is preferably selected so that $H_2$ is used in a stoichiometric excess. This has the advantage that, for example, the conversion of high-boiling silane fractions into monosilanes as described in U.S. Pat. No. 5,292,909 can be carried out without pressure or additional catalysts having to be employed and that maintenance of the flame is simplified. The molar excess of $H_2$ can be varied within a wide range and depends on the desired reaction.

The stoichiometric ratio of Si:HCl when using silicon (a) and Si—Si:HCl based on the Si—Si bonds in the disilanes and oligosilanes (b) can be chosen freely. In a particularly preferred embodiment, the amount of HCl is selected so that no appreciable amounts of HCl are present after the reaction of the reactants is complete. This has the advantage that the work-up after the reaction is simplified.

After leaving the reaction zone, the reaction gas comprising the silanes of the formula 1 is cooled. Cooling can be carried out in one or more stages, and the heat of reaction still to be removed can, if desired, be used (at least in part) for the generation of steam.

When the process is carried out using starting materials comprising reactants (a) and (b) and also appreciable amounts of metals or metal chlorides which are soluble in chlorosilanes, an appropriate step to remove these, as described, for example, in Lewis, *op. cit.*, page 6, is advisable.

When solids-containing starting materials are used, solids generally must be separated after the reaction. Separation can be effected by means of hot gas filtration and/or a solid/liquid filtration after condensation of the silanes of the formula 1. Preference is given to an initial gas/solid separation by means of cyclones with a subsequent liquid/solid filtration after condensation, since this is simple to carry out and is quite effective. In a preferred embodiment, the gas which remains after the condensation is mostly hydrogen, and can be reused for HCl production, although any methane formed is separated off beforehand. Residual HCl does not interfere. The liquid product stream obtained after condensation and filtration consists mainly of silanes of the formula 1 and is passed to distillation. Unreacted silicon-containing starting materials can, if desired, be fed partially or wholly back into the reactor.

The reactants (a) and (b) are introduced either directly into the flame or into the hot HCl gas stream, and they can be fed in tangentially, radially or axially to the flame direction. It is also possible to introduce the reactants (a) and (b) into the reaction zone together with the $H_2$ stream.

The purity of the starting materials comprising the reactants (a) and (b) does not have to meet any particular requirements; they can contain quite a high level of impurities. If silicon metal (a) is used, for example, it is possible to directly use dusts which are obtained in comminution of silicon or ferrosilicon; or silicon-containing dusts which are obtained in the synthesis of chlorosilane or of methylchlorosilane, and which sometimes still contain catalyst constituents such as copper/copper compounds and zinc/zinc compounds. It is also possible to use dry Si-containing residues from the Müller-Rochow process, as are obtained after recovery of Cu. Furthermore, silicon and/or ferrosilicon can be milled to produce feedstock for the process.

Silicon metal (a) is preferably introduced in finely divided form. The silicon used preferably has a particle size of not more than 100 $\mu$m, more preferably not more than 70 $\mu$m, and most preferably not more than 50 $\mu$m.

The silicon metal (a) can contain up to 50% by weight, in particular up to 30% by weight, of other elements. The type and concentration of these elements depends on the reactant stream source. For example, when the silicon metal is derived from dusts from the synthesis of methylchlorosilane, the non-silicon elements are mainly copper, iron and oxygen compounds. Silicon-iron alloys having an iron content of above 5% by weight are usually referred to as ferrosilicon.

When silicon metal (a) is used as reactant, it is preferred that at least 80% by weight of the silanes of the formula 1 obtained are trichlorosilane and tetrachlorosilane.

The disilanes and oligosilanes (b) used as starting material can be solids-containing, and disiloxanes, oligosiloxanes and carbosilanes can further be present.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A concerted process for preparing silanes of the formula 1:

$$R_aSiH_bCl_{4-a-b} \qquad (1)$$

where
R is methyl or ethyl,
a is 0, 1, 2 or 3 and
b is 0 or 1,
from hydrogen chloride gas and reactants selected from among (a) silicon metal, (b) disilanes and/or oligosilanes whose radicals are selected from among H, R and Cl, or mixtures thereof, wherein hydrogen chloride gas is prepared by combusting $H_2$ and $Cl_2$ in the concerted process, and wherein said reactants are introduced together with $H_2$ and $Cl_2$ into a reactor, or into a zone of the reactor, whereby said reactants contact hydrogen chloride still hot from combustion of $H_2$ and $Cl_2$ within the reactor.

2. The process of claim 1, wherein the hydrogen chloride gas is prepared from $H_2$ and $Cl_2$ in a combustion tube.

3. The process of claim 1, wherein further hydrogen chloride gas in addition to the hydrogen chloride gas prepared from $H_2$ and $Cl_2$ in the concerted process is fed in as reactant (c).

4. The process of claim 2, wherein further hydrogen chloride gas in addition to the hydrogen chloride gas prepared from $H_2$ and $Cl_2$ in the concerted process is fed in as reactant (c).

5. The process of claim 3, wherein the amount of further hydrogen chloride gas added is selected so that the temperature in the region of the reaction of hydrogen chloride gas with the other reactants (a) and/or (b) is at least 400° C.

6. The process of claim 4, wherein the amount of further hydrogen chloride gas added is selected so that the temperature in the region of the reaction of hydrogen chloride gas with the other reactants (a) and/or (b) is at least 400° C.

7. A concerted process for preparing silanes of the formula 1:

$$R_aSiH_bCl_{4-a-b} \qquad (1)$$

where
R is methyl or ethyl,
a is 0, 1, 2 or 3 and
b is 0 or 1,
said process comprising:

introducing hydrogen and chlorine into a reactor and combusting therein to form hydrogen chloride;

optionally adding additional, pre-synthesized hydrogen chloride to said reactor to produce a hydrogen chloride composition having a temperature less than the temperature of hydrogen chloride produced by combustion of hydrogen and chlorine;

contacting said hydrogen chloride or said hydrogen chloride composition with a reactant comprising (a) silicon metal, (b) disilanes and/or oligosilanes, or mixtures thereof; and recovering a silane of the formula 1.

8. The process of claim 7, where additional, pre-synthesized hydrogen chloride is added, and the hydrogen chloride composition temperature is greater than 400° C.

9. The process of claim 7, wherein hydrogen is employed in stoichiometric excess relative to chlorine.

10. The process of claim 7, wherein the temperature in said reactor is maintained at a selected value, at least in part by the introduction of a substance inert under the reaction conditions as a cooling medium.

11. The process of claim 10, wherein at least a portion of said substance is a chlorosilane.

12. The process of claim 11, wherein said chlorosilane comprises silicon tetrachloride.

13. The process of claim 1 wherein at least one reactant is admixed with $H_2$, with $Cl_2$, or with both $H_2$ and $Cl_2$ prior to combustion of $H_2$ and $Cl_2$ in the reactor.

14. The process of claim 1 wherein $H_2$ is supplied in stoichiometric excess relative to $Cl_2$.

15. The process of claim 1 wherein said $H_2$ and $Cl_2$ are combusted and reacted with said reactants in a single reaction zone.

16. A concerted process for the preparation of the formula 1:

$$R_aSiH_bCl_{4-a-b} \qquad (1)$$

where

R is methyl or ethyl, a is 0, 1, 2 or 3 and b is 0 or 1, from hydrogen chloride gas and reactants selected from among (a) silicon metal, (b) disilanes and/or oligosilanes whose radicals are selected from among H, R and Cl, or mixtures thereof, wherein hydrogen chloride gas is prepared from $H_2$ and $Cl_2$ in the concerted process, and wherein said reactants are introduced together with $H_2$ and $Cl_2$ into a reactor, or into a zone of the reactor, whereby said reactants contact hydrogen chloride still hot from combustion of $H_2$ and $Cl_2$, and wherein the temperature of HCl still hot from the combustion is reduced from the combustion temperature of $H_2$ and $Cl_2$ to a temperature less than said combustion temperature by the addition of preformed HCl into said reactor.

17. The process of claim 16, wherein said temperature less than said combustion temperature is greater than 600° C.

18. The process of claim 16, wherein said temperature less than said combustion temperature is in the range of 400° C. to 600° C.

19. The process of claim 16, wherein hydrogen is employed in stoichiometric excess relative to chlorine.

* * * * *